United States Patent [19]
Weinshenker et al.

[11] Patent Number: 5,068,226
[45] Date of Patent: Nov. 26, 1991

[54] PHARMACEUTICAL PREPARATIONS CONTAINING CYCLODEXTRINS AND THEIR USE IN IONTOPHORETIC THERAPIES

[75] Inventors: Ned M. Weinshenker, Palo Alto; William P. O'Neill, Los Altos, both of Calif.

[73] Assignee: Cyclex, Inc., New Brunswick, N.J.

[21] Appl. No.: 516,295

[22] Filed: Apr. 30, 1990

Related U.S. Application Data

[63] Continuation of Ser. No. 129,187, Dec. 7, 1987, abandoned.

[51] Int. Cl.$^5$ .................... A01N 43/04; A61F 13/60
[52] U.S. Cl. ............................ 514/58; 536/46; 536/103; 425/449; 604/19; 604/20; 540/2; 252/351

[58] Field of Search .............. 514/58; 536/46, 103; 425/449; 604/19, 20; 540/2; 260/397.45; 252/351

[56] References Cited

U.S. PATENT DOCUMENTS

| | | | |
|---|---|---|---|
| 3,598,122 | 8/1971 | Zaffaroni | 424/435 |
| 3,598,123 | 8/1971 | Zaffaroni | 424/435 |
| 4,379,454 | 4/1983 | Campbell et al. | 424/449 |
| 4,383,992 | 5/1983 | Lipari | 536/103 |
| 4,596,795 | 6/1986 | Pitha | 536/103 |
| 4,834,985 | 5/1989 | Elger et al. | 536/103 |
| 4,877,774 | 10/1989 | Pitha et al. | 514/178 |

Primary Examiner—Ronald W. Griffin
Assistant Examiner—Pamela S. Webber
Attorney, Agent, or Firm—Raymond S. Parker

[57] ABSTRACT

Cyclodextrins and especially ionic cyclodextrin derivatives facilitate the iontophoretic delivery of pharmaceutically active agents.

17 Claims, 2 Drawing Sheets

PHARMACEUTICAL PREPARATIONS CONTAINING CYCLODEXTRINS AND THEIR USE IN IONTOPHORETIC THERAPIES

This application is a continuation of application Ser. No. 07/129,187 filed 12/07/87, now abandoned.

BACKGROUND OF THE INVENTION

1. Field of the Invention

This invention relates to the fields of pharmacology and pharmacodynamics. More specifically, it concerns the use of cyclodextrins to modify the pharmacodynamic properties of pharmaceutically active agents and vary their iontophoretic transport propertires.

2. Background Information

The present invention involves the iontophoretic transport of pharmaceutically active agents. It has long been recognized that under proper conditions pharmaceutically active agents can pass through the body's epithelial layers and enter the patient's circulation. Representative references to this transdermal mode of administration include the following: U.S. Pat. Nos. 3,598,122 and '123 to Zaffaroni and 4,379,454 to Campbell et al.

It has also been recognized that an electrical current can be used to assist or expedite transdermal delivery. This use of electrical currents to drive materials is called iontophoresis or iontophoretic delivery. Representative references to iontophoresis include the following: "Iontophoresis in Dermatology, a Review" by Joanna B. Sloan et al, *Journal of the American Academy of Dermatology* (1986) 671; Louis P. Gangarosa et al, *The Journal of Pharmacology and Experimental Therapeutics* (1980) 212, No. 3, 377, and A. Chantraire et al, *Arch. Phys. Med. Rehabil.* (January, 1986) 67, 38.

The present invention employs cyclodextrins to facilitate these modes of drug delivery. Three textbooks concerning cyclodextrins are *Cyclodextrins and Their Inclusion Complexes* by J. Szejtli (Akademiai Kiado, Budapest, 1982); *Proceedings of the First International Symposium on Cyclodextrins*, edited by J. Szejtli, (D. Reidel Publishing Company, Dordrecht, Holland), and *Cyclodextrin Chemistry*, by M. L. Bender et al (Springer-Verlag, Berlin, 1978). These three references provide a great deal of information on the preparation and properties of the cyclodextrin materials. In certain preferred embodiments of this invention, ionic cyclodextrins are employed. References directed to ionic cyclodextrins include U.S. Pat. Nos. 3,426,011 and 4,535,152.

Although various elements of the present invention have been disclosed as just described, to applicant's knowledge, the art has not described the use of cyclodextrins to facilitate transdermal drug transport or more specifically to assist in the iontophoretic transport of drugs.

STATEMENT OF THE INVENTION

Cyclodextrins have been found to facilitate the iontophoretic delivery of pharmaceutically active agents in two different ways:

1) neutral cyclodextrins which form complexes with ionized agents enable higher concentrations of those agents to be placed in solution and higher fluxes to be achieved under given iontophoresis conditions than could be obtained with saturated aqueous solutions of those ionic agents alone under the same conditions;

2) charge-bearing derivatives of cyclodextrins which form complexes with drugs can be used to transport those drugs through the skin under iontophoretic conditions at much faster rates than those drugs themselves are capable of migrating under the same conditions in the absence of the cyclodextrin derivatives.

Thus in one aspect the present invention provides a pharmaceutical preparation for enhanced iontophoretic administration of an active agent to a mammalian patient. This preparation includes an effective concentration of the active agent dispersed in a water-containing fluid medium and in admixture therewith cyclodextrin.

In a preferred aspect the present invention provides such a pharmaceutical preparation wherein the cyclodextrin is an ionic cyclodextrin.

In another aspect the present invention concerns the method of iontophoretically medicating a patient using such preparations. Such methods in their broadest sense involve iontophoretically driving an effective amount of the active agent across an epithelial surface of a mammalian patient using cyclodextrin-containing preparations as the source of the active agents.

Such method comprises the steps of contacting an epithelial surface of the patient with such a preparation, applying across the epithelial surface in contact with said preparation an electrical current effective to bring about iontophoretic transport of the pharmacologically active agent across the epithelial surface into the patient's body.

DETAILED DESCRIPTION OF THE INVENTION

Brief Description of the Drawings

The present invention will be described with reference being made to the accompanying drawings in which.

DESCRIPTION OF PREFERRED EMBODIMENTS

The Cyclodextrins

The present invention relies upon cyclodextrins to facilitate the iontophoretic administration of active agent to patients.

The cyclodextrins are a group of homologous oligosaccharides that are obtained from starch by the action of enzymes elaborated by *Bacillus macerans*. They are cyclic molecules containing six or more alpha-D glucopyranose units linked together at the 1,4 positions as in amylose.

Figure 1:
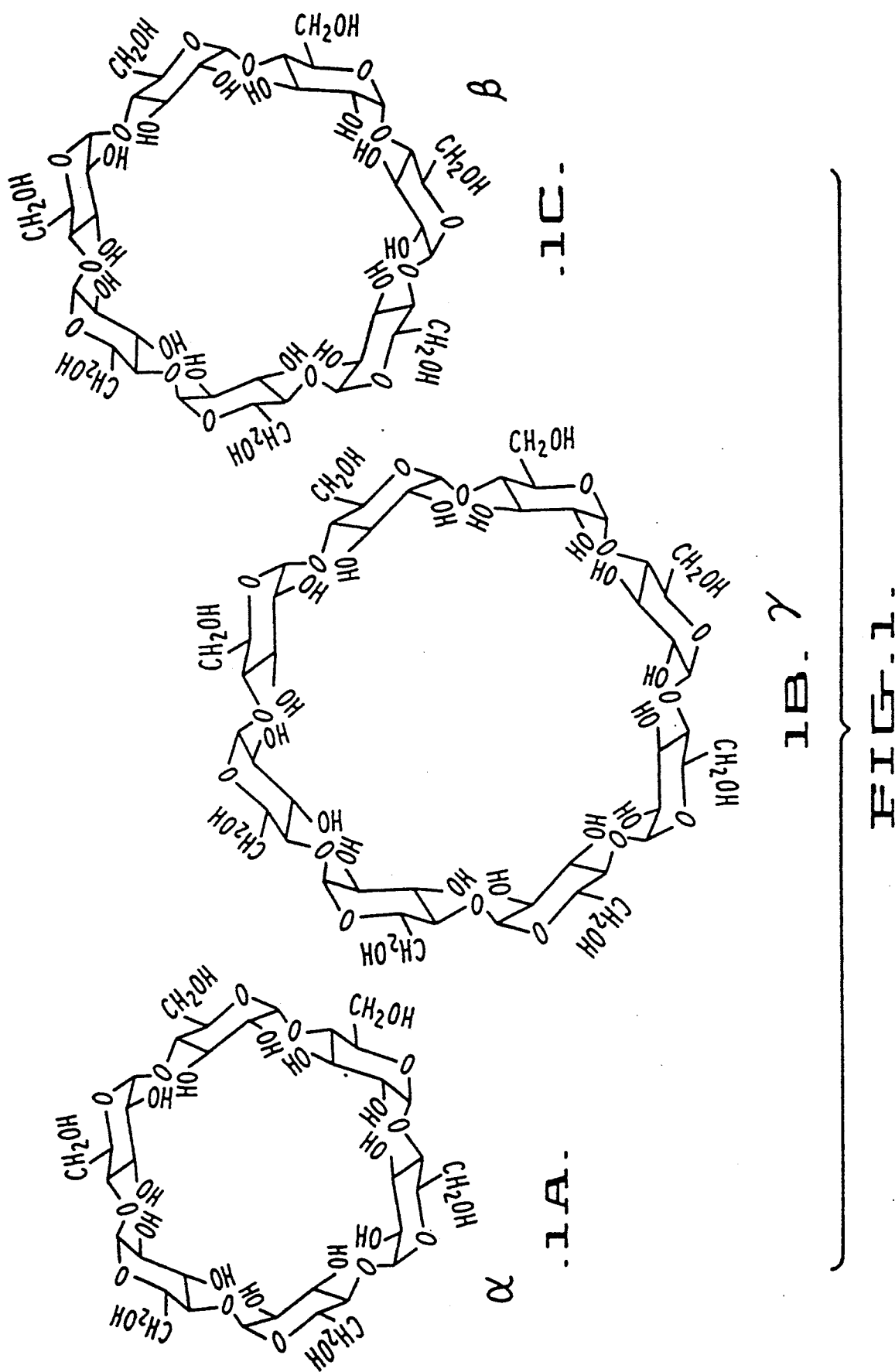
FIGS. 1A, 1B and 1C are a series of structural chemical formulae of three representative underivatized cyclodextrins useful in accordance with this invention.

This cyclic structure may also be referred to as a torus. FIGS. 1A, B and C show the structures of the three smallest cyclodextrins—alpha having 6 glucopyranose units, beta having 7 glucopyranose units, and gamma having 8 glucopyranose units. Mixtures of these materials are included in the term "cyclodextrin" as used herein.

In addition to the natural cyclodextrins a wide range of derivatives are also known.

Systematic names for derivatized cyclodextrins are exceedingly complicated. For instance, a beta-cyclodextrin in which primary hydroxyl groups are substituted by amino groups and the rest of hydroxyls are acetylated, should be described systematically as 2,2', 2'',2''',2'''',2''''',2'''''',3,3',3'',3''',3'''',3''''', 3''''''-[tetradecaacetyl-6,6',6'',6''',6'''',6''''', 6''''''-heptaamino-6,6',6'',6''',6'''',6''''',6''''''-heptadeoxy-beta-cyclodextrin (cf., e.q., *Chem. Abstracts, 8th Coll. Subject Index*, 1967–71), American Chemical Society, Columbus, Ohio, 1972, pp. 8952–8953). In the present application, however, the much simpler name tetradecakis-(2,3-O-acetyl)-heptakis-(6-deoxy-6-amino)-beta-cyclodextrin will be used.

Alpha-cyclodextrin contains 18 hydroxyl groups and beta-cyclodextrin contains 21 hydroxyl groups, of which the primary ones (six and seven, respectively) are the most reactive. Hydroxyls located on the secondary carbons, i.e., the ones at C-2 and C-3, also show a marked difference in their reactivity; the hydroxyls at C-3 are much less reactive than those at C-2. These hydroxyl groups are all possible derivatization points.

Derivatives include, for example, cyclodextrins substituted with: non-ionic groups, such as esters, ethers, desoxyamino groups and the like, and ionizable groups, such as carboxyls, sulphoxyls, quaternary ammonium salts, and the like. Representative descriptions of derivatives and their preparation include the following: Early literature has been reviewed by French (1957), *Adv. Carbohydr. Chem.* 12:189, and work, published through June 1981, has been reviewed by Croft and Bartsch (1983), *Tetrahedron* 39:1417. More recently Pitha (1986), *Int. J. of Pharmaceutics* 29:73, has reported hydroxypropyl derivatives and other amorphous derivatives which markedly enhance water solubility of hydrophobic drugs.

Non-ionic derivatives of cyclodextrins are of interest in the present context primarily because they are often more water soluble than the parent cyclodextrins. Thus, for example, hydroxypropyl derivatives of betacyclodextrin, prepared by condensation of the cyclodextrin with propylene oxide, are far more soluble and increase the solubilities of drugs, such as steroids, by several orders of magnitude. Production of a variety of such derivatives, by condensation of different epoxides with various cyclodextrins, is described by Pitha and Pitha (1985), *J. Pharm. Sci.* 74:987. Other non-ionic derivatives, such as heptakis-(2,6-O-dimethyl)betacyclodextrin, prepared by treatment with dimethyl sulfate and barium oxide as described by Casu et al (1968), *Tetrahedron* 24:803, also are more soluble than the parent compounds and have been shown to increase the water solubility of hydrophobic compounds, such as the anti-inflammatory drug flurbiprofen, in linear proportion to the concentration of the cyclodextrin derivative.

Another aspect of non-ionic cylcodextrin derivatives is that they may serve as intermediates in the preparation of charged cyclodextrin derivatives. For example, one may treat alpha-cyclodextrin with p-toluenesulphonyl chloride, to produce the hexakis-(6-O-ptoluenesulphonyl) derivative. Purification is necessary if it is desired to obtain only that product since the reaction cannot be stopped precisely after the acylation of only the primary hydroxyl groups. By reacting with suitable nucleophiles, the p-toluenesulphonate can be converted to various desoxy substituents. Thus, for example, a 6-amino-6-desoxy derivative can be obtained by conversion with azide ion, followed by reduction (Umezawa and Tatsuta, 1968, *Bull. Chem. Soc. Jpn.* 41:464). Reaction of a mono-tosylate of beta-cyclodextrin with trimethylamine in dimethylformamide can be used to obtain a quaternary trimethylammonium substituted cyclodextrin directly (Matsui and Okimota, 1978, *Bull. Chem. Soc. Jpn.* 51:3030).

Numerous charged cyclodextrin derivatives, which it has now been found are useful for promoting the transport of drugs through epithelial tissue under iontophoresis conditions, have been prepared by various means. For example, the addition of monochloroacetic acid to an alkaline solution of alpha- or beta-cyclodextrin has been used to obtain cyclodextrincarboxymethylether sodium salts (Lammers et al, 1971, *Die Staerke* 23:167). The same publication describes the preparation of cyclodextrinsulfopropylether sodium salts, by addition of liquid propane sulfone to alkaline cyclodextrin solutions.

Treatment of cyclodextrins with various cyclic anhydrides yields mixtures of cyclodextrin derivatives with pendant carboxylic acid groups (Parmeter and Allen, U.S. Pat. No. 3,453,260, 1969). Treatment of the parent cyclodextrin with sodium iodoacetate in dimethylsulfoxide produces mono [2(3)-O-(carboxymethyl)]-alpha-cyclodextrin (Bender et al, 1974-5, *Biorg. Chem.* 3:324 and 4:237). Oxidation, with either platinum and oxygen or nitrogen oxide, of all of the primary hydroxyl groups in the parent cyclodextrins can be used to obtain hexakis(5-carboxy-6-deoxy-5-demethyl)alpha and beta cyclodextrins (Casu et al, 1968, *Carbohydr. Res.* 63:13).

Monophosphoryl beta-cyclodextrins can be prepared through reaction of diarylpyrophosphates and the parent cyclodextrins (Hennrich and Cramer, 1965, *J. Am. Chem. Soc.* 87:1121, and Siegel et al, 1977, *J. Am. Chem. Soc.* 99:2309). Trisubstituted phosphoryl derivatives have been synthesized by analogous methods in the presence of a large excess of diphenylphosphorochloridate (Van Hooidonk et al, 1970, *Recl. Trav. Chim. Pays-Bas* 89:289 and 845).

The trimethylammonium salt of alpha-cyclodextrin polysulfate, hexakis(2,3,6,tri-O-sulfo)-alpha-cyclodextrin has been prepared by treatment of the parent cyclodextrin with triethylammonium sulfonate in dimethylformamide (Bernstein et al, U.S. Pat. No. 4,020,160, 1977)

Parmeter et al (U.S. Pat. No. 3,453,257, 1969) obtained ionized quaternary ammonium ether cyclodextrins by reaction of the parent cyclodextrin with a quaternary ammonium-substituted epoxide reagent.

These various disclosures of cyclodextrin derivatives and their preparation are incorporated by reference.

Iontophoretic Conditions

The iontophoretic conditions employed herein to achieve active agent transport include a continuous or a pulsed direct electric current, generally in the ma/cm$^2$ range from about 0.1 to about 5 ma/cm$^2$. Currents from about 0.2 to about 2 ma/cm$^2$ are preferred. The voltage employed can range up to about 40 volts, with voltages from about 8 to about 35 volts being preferred. As will be appreciated, the voltage and current achieved will vary as a function of the resistance of the contact with the patient's epithelial surface. This could lead to fluctuations and surges in voltage or current. These variations are very undesirable because they can cause shock or, at minimum, discomfort to the patient. They can, however, be minimized by the use of an interactive power supply which can control and eliminate the variations as is known to the art. Such a system is shown, for example in U.S. Pat. No. 4,141,359 of Jacobson et al which is incorporated herein by reference. Another improvement in the electronics of iontophoresis is shown by Okabe et al in *Journal of Controlled Release* Vol 4 (1986) 79-85. This article illustrates the advantage of using a relatively high frequency (50 KHz) pulsed current.

Other variables to be controlled in the iontophoretic delivery regimen include the area of epithelial tissue contacted by the electrodes and the duration of delivery with the amount of active agent administered being directly proportional to each of these variables. Typical surface areas range from about 0.25 $cm^2$ to about 400 $cm^2$, with areas from about 1 cm to about 100 $cm^2$ being preferred. Administration times can vary from a few minutes to many hours, depending upon the effect desired and the active agents employed. Representative treatment periods range from about 10 minutes to about 48 hours. Continuous iontophoretic delivery is also possible.

Figure 2:
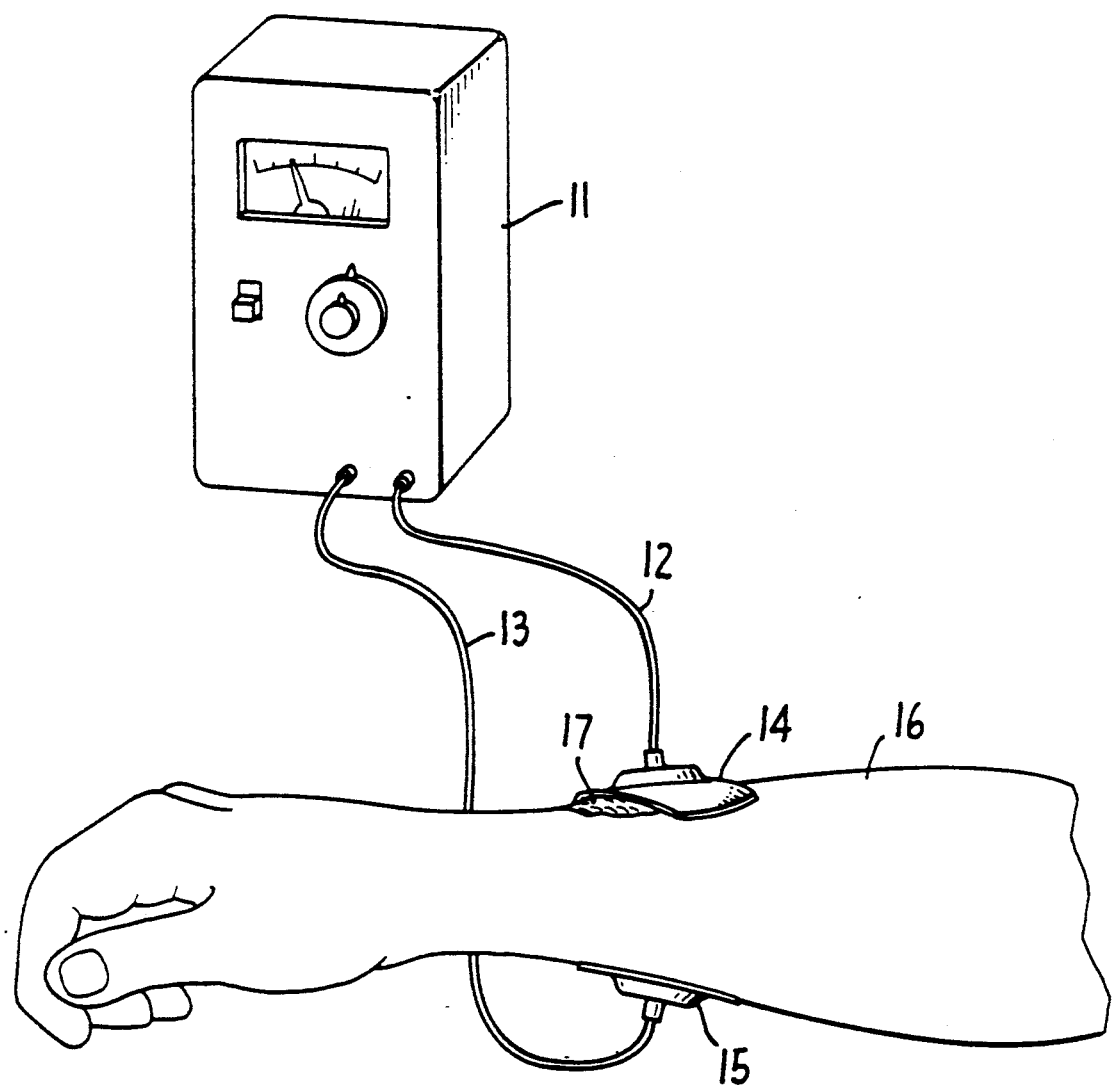
FIG. 2 is a schematic representation of an iontophoretic transport system for delivering active agent to a patient.

FIG. 2 illustrates a typical setup for iontophoretically administering an active agent to a patient. It includes a power supply 11 capable of delivering a controlled direct current output, either continuous or pulsed. Leads 12 and 13 run from the power supply to electrodes 14 and 15, shown positioned on patient 16. Drug composition 17, which includes the cyclodextrin, is applied to patient 16 as a salve or other fluid. Electric current from supply 11 drives the drug into the patient.

The polarity of the output is set depending upon the charge characteristics of the formulation. If the drug and cyclodextrin complex is positively charged, electrode 15 will be negatively charged to attract it while electrode 14 will be positively charged to drive it into the skin.

Figure 3:
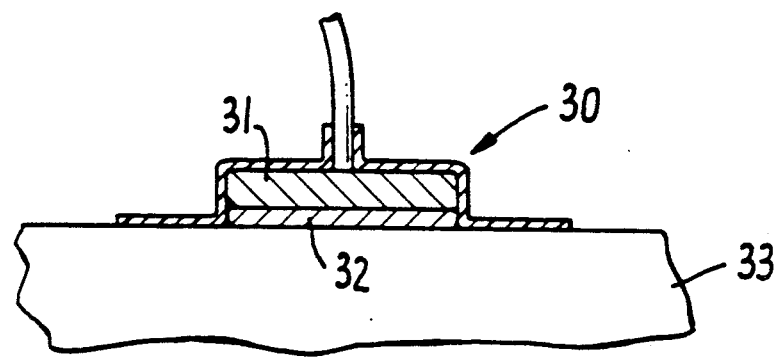
FIG. 3 is a cross-sectional view of a depot-containing iontophoretic electrode which can be used in the methods of this invention.

FIG. 3 shows an electrode 30 design in which the cyclodextrin/drug mixture is lodged in a depot 31. Depot 31 is enclosed in a permeable wall so that drug complex can be driven through it and delivered to patient 33.

The use of the present invention provides a number of advantages. For one, it can increase the solubility of the active agent in the carrier liquid. This increase in concentration has the direct effect of increasing the rate of iontophoretic transport. For another, when ionic cyclodextrins are employed, the invention can add charge to drugs which are neutral or weakly ionized, by the formation of a complex with a net electrical charge that will enhance transport of the drug under iontophoresis conditions. For another, the cyclodextrins themselves are substantially inert to the epithelial tissues with which they are contacted. This means that they can minimize irritation which might occur during prolonged contact between these surfaces and irritating active agents.

The cyclodextrins can also serve to stabilize or protect the drug being delivered. Drugs, when complexed with cyclodextrins, have been shown to have increased stability against hydrolysis, oxidation and photodegradation. This will allow the manufacture of hydrated systems with long shelf lives.

Active Agent-Containing Compositions

The compositions which are administered iontophoretically contain a carrier liquid, one or more cyclodextrins and one or more active agents.

The carrier liquid is an aqueous liquid or water-containing liquid mixture. Typical constituents can include water, lower alcohols such as methanol or ethanol or isopropanol, glycols and other polyols such as ethylene glycol or propylene glycol, ketones such as acetone and the like, DMSO and the like. Usually the carrier liquid will be at least about 50% by volume water and more preferably at least about 80% by volume water. In many cases water is a very suitable carrier liquid. In selecting the carrier liquid components as well as any of the other possible constituents, care should be taken to select materials which are physiologically compatible and nontoxic as used.

The compositions can contain a variety of optional excipients known in the art. These can include gelling agents such as the natural and synthetic gums, and colloids, for example gelatin, gum arabic, polyacrylamide gels, guar gum and the like if a gelled product is desired. They can also contain salts and the like to increase their conductivity.

The active agents which can be delivered in accord with the present invention can be selected broadly from the class of materials which will bring about a desired physiologic effect in a patient when administered iontophoretically. These include (without limitation) the steroids, which are often only marginally soluble but have greatly enhanced solubility when cyclodextrins are present (generally over 100-fold increase). For example, testosterone's solubility can be increased 1500-fold, progesterone 2000-fold and estradiol 5000-fold (from 0.004 mg/ml to 28 mg/ml). Similar effects are observed with other steroids such as prednisolone and hydrocortisone.

Other representative drugs which may be administered advantageously by means of iontophoresis augmented with cyclodextrins include alpha-adrenergic blocking agents, such as clonidine; beta-adrenergic blocking agents, such as pindolol; anesthetics, such as lidocaine; anti-inflammatory agents, such as piroxicam; antiviral agents, such as vidarabine; cardiovascular agents, such as nitroglycerin; alkaloids, such as ergotamine, and lipid hormones such as prostaglandins.

As can be seen by the wide range of materials listed here, the invention has universal application and is not limited to any particular type or family of active agents or drug materials.

Typical compositions will have the following makeup:

| | |
|---|---|
| Cyclodextrins | 0.1 to 60% w |
| Active agent | 10 ppm to 20% w |
| Optional Ingredients | 0 to 10% w |
| Carrier Liquid | Q.S. |

Preferred compositions will have the following makeup:

| | |
|---|---|
| Cyclodextrins | 1 to 60% w |
| Active agent | 100 ppm to 15% w |
| Optional Ingredients | 0 to 3% w |
| Carrier Liquid (50+% $H_2O$) | Q.S. |

More preferred compositions will have the following makeup:

| | |
|---|---|
| Ionic Cyclodextrins | 3 to 60% w |
| Active agent | 100 ppm to 15% w |
| Optional Ingredients | 0 to 3% w |

| | |
|---|---|
| -continued | |
| Carrier Liquid (50+% H₂O) | Q.S. |

The invention will be further described by the following examples. These are provided merely to illustrate the invention and are not to be construed as limiting its scope.

EXAMPLE 1

Carboxymethyl beta-cyclodextrin sodium salt, prepared according to the methods of Lammers (1971), is dissolved in water to create a 25% weight solution. Testosterone (15 mg) dissolved in 1 ml of this solution becomes complexed by the negatively charged cyclodextrin derivative and is rendered more than two orders of magnitude more soluble than it is in water alone. When this material is placed in a depot as shown in FIG. 3 and iontophoretically administered as shown in FIG. 2 at 12 volts and about 0.5 ma/cm$^2$ of electrode area, it would be expected that reproducibly elevated levels of testosterone can be detected in the bloodstream by radioimmunoassay of serum samples. Considerable variation would be observed for different individuals and for different body surfaces on the same individual. After the electric potential source is disconnected, attained levels of testosterone would diminish, and would rise again when power is restored.

In the absence of the charged derivative of cyclodextrin, that is when the depot is filled either with a saturated aqueous solution of testosterone or with a solution of testosterone in saturated aqueous beta-cyclodextrin, no significant absorption of testosterone would be seen to occur.

EXAMPLE 2

Aqueous carboxymethyl beta-cylcodextrin sodium salt (25% weight) can also be used to prepare formulations for iontophoresis of the uncharged antiviral agent, vidarabine (Ara-A). Drug penetration into mouse skin can be monitored through the attachment of a tritium-label on the drug. To monitor the drug transport one could do the following. After (24 hr) removal of the hair from dorsal trunk surfaces of anesthetized adult mice with depilatory cream (Surgex®), labeled drug solution ([3H]-Ara-A, New England Nuclear Co., Boston, Mass.; specific activity approximately 18 microCi/mM; 25 microCi/ml) is applied to an area of the skin large enough for the attachment of cotton wick electrodes (surface area 35 mm$^2$) saturated with the drug solution. Current (0.5 ma/cm$^2$) is applied for 10–60 minutes.

Drug is thoroughly washed off the skin area with running distilled water and, 10 minutes after iontophoresis, the mice are sacrificed by cervical dislocation. Skin samples are taken by the punch biopsy method. Weighed punch specimens from comparable skin areas of a plurality of mice for each treatment are pooled and homogenized in 0.5 N perchloric acid. Homogenates are centrifuged and aliquots of the supernatant fraction are mixed with Triton scintillation cocktail solution for counting in a liquid scintillation counter.

Skin samples from areas not subjected to iontophoresis, but treated for the same period of time either with the labeled solution of Ara-A in aqueous carboxymethyl cyclodextrin or with a saturated aqueous solution of labeled Ara-A are also assayed. After washing, these areas of topical treatment, never subjected to iontophoresis, seldom show a disintegration count level in excess of 200 cpm/mg wet tissue.

The skin specimens taken from areas under the iontophoresis cathodes would be expected to contain more than one thousand cpm/mg of wet tissue, about fivefold greater than the cpm/mg of skin taken from beneath the anodic electrodes. This result would demonstrate that the cathode drives drug into the skin when the drug is presented in a complex derived from an anionic cyclodextrin derivative and iontophoresis conditions are established. Such a combination may be used in the treatment of viral lesions, through which the penetration of the unaided drug is poor.

EXAMPLE 3

The enhancement of iontophoretic penetration of skin by charged drugs in the presence of cyclodextrins may be demonstrated in the following manner. Solutions of prednisolone sodium phosphate in either 50% weight 2-hydroxypropyl beta-cyclodextrin, prepared according to the methods of Pitha (1985) or in water, would be placed in an electrode depot, as shown in FIG. 3, that is attached to the abdomen. Iontophoresis (0.2–0.3 ma/cm$^2$) is carried out for 10–15 minutes. Control areas are treated with the same drug solutions but no electric current is applied to those areas. The skin in all of the areas is rinsed thoroughly with running water for five minutes after the treatments.

Twenty-four hours later a suction blister is raised on each treated site. The roof of the blister (epidermis) is detached, and the underlying dermis is sampled by punch biopsy, after infiltrating the surrounding skin with local anesthetic. An adjacent biopsy of whole skin is taken from the treated area at the same time. Samples are weighed, homogenized and extracted with ethyl acetate. Extracts are assayed for prednisolone by radioimmunoassay.

Prednisolone concentrations in the tissues treated under iontophoresis conditions would be seen to far exceed the background levels of topically treated skin. The range from one patient to another would be quite large for comparable tissues in the iontophoresis experiments, but on average the levels attained with the formulations containing hydroxypropyl beta-cyclodextrin would exceed those obtained from the aqueous drug solutions by a substantial amount. In one subject, for example, prednisolone levels (ng/mg wet tissue weight) of 42,000, 400 and 33,000, respectively, for epidermis, dermis and whole skin would be obtained with 5% aqueous drug, and each of these levels would be expected to be at least 50% greater when the same individual is treated with the drug dissolved in aqueous hydroxypropyl beta-cyclodextrin. In another individual all of the tissue prednisolone levels may be as much as an order of magnitude lower, but the relative levels in the presence and absence of cyclodextrin derivative would bear a similar relationship, favoring the composition containing the cyclodextrin derivative.

What is claimed is:

1. A method for the iontophoretic administration of a pharmacologically active agent to a mammalian patient comprising:
   (a) contacting an epithelial surface of the patient with a pharmaceutical preparation comprising:
      (i) a cyclodextrin;
      (ii) an effective concentration of the pharmacologically active agent that forms with the cyclodextrin an inclusion complex having a net ionic charge;

(iii) a water-based fluid carrier medium in which the active agent is dispersed and in admixture with the cyclodextrin; and thereafter (b) applying to the preparation on the surface an electrical current effective to bring about iontophoretic transport to the pharmacologically active agent across the surface into the patient's body.

2. The method of claim 1 wherein the cyclodextrin comprises ionic cyclodextrin.

3. The method of claim 1 wherein the cyclodextrin comprises nonionic cyclodextrin.

4. The method of claim 1 wherein the active agent is substantially uncharged.

5. The method of claim 1 wherein the active agent has limited water solubility.

6. The method of claim 2 wherein the active agent is substantially uncharged and the ionic cyclodextrin that forms the inclusion complex with the active agent thereby imparts the net ionic charge to the complex.

7. The method of claim 1 wherein the cyclodextrin comprises alpha-cyclodextrin, beta-cyclodextrin or gamma-cyclodextrin.

8. The method of claim 1 wherein the cyclodextrin comprises alpha-cyclodextrin.

9. The method of claim 1 wherein the cyclodextrin comprises beta-cyclodextrin.

10. The method of claim 1 wherein the cyclodextrin comprises gamma-cyclodextrin.

11. The method of claim 2 wherein the ionic cyclodextrin is an alpha-cyclodextrin and the active agent includes a hydrophobic moiety having four or more atoms which can serve as a ligand to form the inclusion complex with the alpha-cyclodextrin.

12. The method of claim 2 wherein the ionic cyclodextrin is a beta-cyclodextrin, and the active agent includes a hydrophobic moiety which can serve as a ligand to form the inclusion complex with the beta-cyclodextrin.

13. The method of claim 2 wherein the ionic cyclodextrin is a gamma-cyclodextrin and the active agent includes a hydrophobic moiety which can serve as a ligand to form the inclusion complex with the gamma-cyclodextrin.

14. The method of claim 13 wherein the active agent comprises a steroid.

15. The method of claim 14 wherein the active agent comprises a hydrocorticoid steroid.

16. The method of claim 2 wherein the ionic cyclodextrin has a net anionic charge.

17. The method of claim 2 wherein the ionic cyclodextrin has a net cationic charge.

* * * * *